United States Patent [19]

Su

[11] Patent Number: 5,136,035

[45] Date of Patent: Aug. 4, 1992

[54] CATALYTIC SYNTHESIS OF ALKYL MORPHOLINONES

[75] Inventor: Wei-Yang Su, Austin, Tex.

[73] Assignee: Texaco Chemical Company, White Plains, N.Y.

[21] Appl. No.: 825,907

[22] Filed: Jan. 27, 1992

[51] Int. Cl.$^5$ ............................................ C07D 265/32
[52] U.S. Cl. ................................................... 544/173
[58] Field of Search ........................................ 544/173

[56] References Cited

U.S. PATENT DOCUMENTS 3,073,822  1/1963  Schultz et al. ................... 544/173
3,324,123  6/1967  Cenker ............................. 544/172

*Primary Examiner*—Robert W. Ramsuer
*Attorney, Agent, or Firm*—Jack H. Park; Kenneth R. Priem; Carl G. Ries

[57] ABSTRACT

4-Alkyl-2-morpholinones are prepared by bringing an N-alkyldiethanolamine into contact with a zinc oxide promoted copper catalyst in the presence of hydrogen under reaction conditions including a temperature within the range of about 240° to about 400° C. and a pressure within the range of about 0 to about 300 psig and by recovering the 4-alkyl-2-morpholinone that is formed by the reaction.

8 Claims, No Drawings

CATALYTIC SYNTHESIS OF ALKYL MORPHOLINONES

BACKGROUND OF THE INVENTION

1. Technical Field of the Invention

This invention relates to a process for preparing 4-alkyl-2-morpholinones from N-alkyldiethanolamines. More particularly, this invention relates to a process for the preparation of 4-alkyl-2-morpholinones in good yield and selectivity by bringing a N-alklyldiethanolamine into contact with a zinc oxide promoted copper catalyst in the presence of hydrogen.

The 4-alkyl-2-morpholinones are useful as intermediates for the preparation of surfactants as shown, for example, in U.S. Pat. No. 4,228,096 and are also useful as solvents.

2. Prior Art

Cenker U.S. Pat. No. 3,324,123 discloses a method for preparing substituted morpholones by contacting a substituted diethanolamine with a reduced copper hydrogenation/dehydrogenation catalyst such as a copper chromite catalyst containing 40 to 85 wt. % of CuO and about 60 to 15 wt. % of $Cr_2O_3$.

Laurent and Bearn in an article entitled "The Reactions of Glyoxal with Amino-Alcohols" (*Bull. Soc. Chim. Fr.* 83 (1978 II), pp. 83–88) disclose the reaction of glyoxal with N-alkylaminoethanols. They report that they obtained about a 40% yield of N,N'-disubstituted-3,3'-dioxazolidines instead of the expected 2-formyl oxazolidine because of the concommitment formation of N-alkyl-2-morpholones, N-alkyl, N-(2-hydroxyethyl-)acetic acids and N-alkyl-2,3-epoxy morpholines.

Schultz et al. U.S. Pat. No. 3,073,822 is directed to a process for the preparation of 4-substituted-2-morpholones by the hydrogenation of N-substituted-dialkanolamines in vapor phase in the presence of a catalyst.

Haas U.S. Pat. No. 4,695,630 is directed to a process for the preparation of polycyclic acetals by the reaction of 2,3-dihydroxydioxane with a 1,2-amino alcohol in an inert solvent.

Jankowski and Berse in a paper entitled "Preparation of Novel Derivatives of Morpholone-2" (*Canadian Journal of Chemistry*, Vol. 46, 1968, pp. 1939–1942) disclose a process wherein an amine acid is reacted with an epoxide to give a morpholone-2 compound.

Vieles and Galsomias in a paper published in the Bulletin of the Chemical Society of France (*Bull. Soc. Chim. Fr.*, 1970, pp. 2529–2534) disclose a process wherein amino alcohols are reacted with halogen esters.

In an article entitled "High-Yield Syntheses of N-(2-Hydroxyethyl)-N-alkylglycine Derivatives by Reaction of Ethanolamines with Glyoxal", Synthesis, 927–929 (1987), Farfan et al. disclose the reactionof N-alkylethanolamines with glyoxal to provide high yields of N-(2-hydroxyethyl)-N-alkylglycine derivatives by conducting the reaction at an elevated temperature of about 70° C.

In copending Su application Ser. No. 07/596,642, filed Oct. 12, 1990, now U.S. Pat. No. 5,066,804 and entitled "Preparation of Alkyl Morpholinones" a process is disclosed for the preparation of 4-alkyl-2-morpholinones in good yield and selectivity by reacting a N-alklylmonoethanolamine with glyoxal.

SUMMARY OF THE INVENTION

The present invention is directed to a method for the preparation of 4-alkyl-2-morpholinones from N-alkyldiethanol amine.

It has been discovered in accordance with the present invention that a significant improvement in yield and selectivity can be obtained if a N-alklyldiethanolamine is brought into contact with a zinc oxide promoted copper catalyst in the presence of hydrogen under reaction conditions including a temperature within the range of about 240° to about 400° C. and a pressure of about 0 to about 300 psig.

DESCRIPTION OF THE PREFERRED EMBODIMENT

The starting materials for the present invention is an N-alkyldiethanolamine wherein the alkyl group contains 1 to 4 carbon atoms.

Representative N-alkyldiethanolamines that can be used as starting materials for the process of the present invention include compounds such as N-methyldiethanolamine, N-ethyldiethanolamine, N-isopropyldiethanolamine, etc.

The reaction conditions to be used in conducting the process of the present invention include a temperature within the range of about 240° to about 400° C. and a pressure of about 0 to about 200 psig. More preferably, the reaction will be conducted at a temperature within the range of 260° to about 330° C. at about atmospheric pressure.

The zinc oxide promoted copper catalyst is preferably used in the form of a fixed bed of particulate catalyst and the N-alkyldiethanolamine feedstock is suitably passed through the bed at a space velocity within the range of about 0.5 to about 3 g of feedstock per cc of catalyst per hour.

Hydrogen should be used. For example, the hydrogen may be passed through the bed of catalyst at a space velocity of about 5 to about 200 volumes of hydrogen per volume of catalyst per hour, and more preferably at the rate of about 25 to about 150 volumes of hydrogen per volume of catalyst per hour.

Typically, conversion of the N-alkyldiethanolamine will be in excess of 95% (e.g., 97% to 100%) and selectivity of the N-alkyldiethanolamine to the corresponding N-alkylmorpholinone will also be in excess of 95% (e.g., 97% to 99%).

The catalyst to be used in accordance with the present invention is a zinc oxide promoted copper catalyst. Zinc oxide promoted copper catalysts are available commercially. Other metal oxide supports such as alumina can also be used in combination with zinc oxide. For example, the catalyst may be composed of from about 0 to about 20 wt. % of alumina, about 5 to about 50 wt. % of zinc oxide, and about 40 to 85 wt. % of copper oxide.

SPECIFIC EXAMPLES

The invention will be further illustrated by the following specific examples which are given by way of illustration and not as limitations on the scope of the invention.

The tests were carried out in a 550 cc Dowtherm ® heated, stainless steel tubular down-flow reactor which had an inside diameter of 1.338" and a thermowell fabricated from ¼-inch O.D. tubing extended upward into the catalyst bed. About 200 cc of the catalyst was charged into the bottom of the reactor, and 300 cc of glass beads was packed on top of the catalyst area to serve as a preheat zone. The catalysts were reduced under the standard conditions.

EXAMPLE 1

CuO—ZnO Catalyst (6678-82)

N-methyldiethanolamine (MDEA) was fed at WHSV of 0.91 g/hr-cc catalyst, atmospheric pressure, and 300° C. (Dowtherm ® temperature). Hydrogen was fed at a rate of 20 liters per hour. The products were collected. GLC analysis showed that a 98% selectivity of 4-methyl-2-morpholinone with a >99% conversion of N-methyldiethanolamine was obtained.

EXAMPLE 2

CuO—ZnO—Al$_2$O$_3$ Catalyst (6770-6)

The procedure of Example 1 was followed except that a (CuO—ZnO—Al$_2$O$_3$) catalyst was used and temperature was at 280° C. GLC analysis showed that a 95% selectivity of 4-methyl-2-morpholinone with >99% of MDEA conversion was obtained.

EXAMPLE 3

Engelhard Cu-1107 Catalyst (6770-19)

The procedure of Example 3 was followed except that Engelhard Cu-1107 catalyst (CuO—Cr$_2$O$_3$) was used. The catalyst contained 75 wt. % CuO, 10 wt. % ZnO and 15 wt. % Al$_2$O$_3$. GLC analysis showed that a 96% selectivity of 4-methyl-2-morpholinone with a >99% of MDEA conversion was obtained.

EXAMPLE 5

6770-30

The procedure of Example 2 was followed. About 8 kg of crude 4-methyl-2-morpholinone was collected. The product was fractionally distilled (b.p. 88° C./0.42 mmHg) to give 90% yield of 4-methyl-2-morpholinone.

Having thus described my invention, what is claimed is:

1. A method for the preparation of a 4-alkyl-2-morpholinone which comprises bringing a N-alkyldiethanolamine into contact with a zinc oxide promoted copper catalyst in the presence of hydrogen and recovering the 4-alkyl-2-morpholinone formed by the reaction.

2. A method as in claim 1 wherein N-alkyldiethanolamine is N-methyldiethanolamine.

3. A method for the preparation of a 4-alkyl-2-morpholinone which comprises bringing an N-alkyldiethanolamine into contact with a zinc oxide promoted copper catalyst in the presence of hydrogen under reaction conditions including a temperature within the range of about 240° to about 400° C. and a pressure within the range of about 0 to about 300 psig and recovering the 4-alkyl-2-morpholinone formed by the reaction.

4. A method as in claim 3 wherein zinc oxide promoted copper catalyst is a catalyst containing about 5 to about 50 wt. % of zinc oxide.

5. A method as in claim 3 wherein zinc promoted copper catalyst is a supported catalyst containing about 40 to about 85 wt. % of copper oxide, about 5 to about 50 wt. % of zinc oxide, and about 0 to about 20 wt. % of alumina.

6. A method as in claim 3 wherein N-alkyldiethanolamine is N-methyldiethanolamine.

7. A method for the preparation of a 4-methyl-2-morpholinone which comprises bringing an N-methyldiethanolamine feedstock into contact with a particulate bed of a zinc oxide promoted copper catalyst in the presence of hydrogen under reaction conditions including a temperature within the range of about 240° to about 400° C., a pressure within the range of about 0 to about 300 psig, an N-methyldiethanolamine flow rate of about 0.5 to about 3 g of feedstock per cc of catalyst per hour, a hydrogen flow rate of about 5 to about 200 volumes of hydrogen per volume of catalyst per hour, and recovering the 4-alkyl-2-morpholinone formed by the reaction.

8. A method as in claim 7 wherein zinc promoted copper catalyst is a supported catalyst containing about 40 to about 85 wt. % of copper oxide, about 5 to about 50 wt. % of zinc oxide, and about 0 to about 20 wt. % of alumina.

* * * * *